(12) United States Patent
Caron et al.

(10) Patent No.: US 7,763,437 B1
(45) Date of Patent: Jul. 27, 2010

(54) METHODS FOR IDENTIFYING COMPOUNDS THAT REGULATE β-ARRESTIN SIGNALING COMPLEXES

(75) Inventors: Marc G. Caron, Hillsborough, NC (US); Martin Beaulieu, Durham, NC (US); Raul R. Gainetdinov, Chapel Hill, NC (US); Tatiana D. Sotnikova, Chapel Hill, NC (US); Sébastien Marion, Durham, NC (US)

(73) Assignee: Duke University, Durham, NC (US)

( * ) Notice: Subject to any disclaimer, the term of this patent is extended or adjusted under 35 U.S.C. 154(b) by 959 days.

(21) Appl. No.: 11/482,277

(22) Filed: Jul. 7, 2006

Related U.S. Application Data

(60) Provisional application No. 60/699,651, filed on Jul. 15, 2005.

(51) Int. Cl.
*G01N 33/53* (2006.01)

(52) U.S. Cl. ............... 435/7.2; 435/4; 435/7.21; 435/7.23; 435/7.24

(58) Field of Classification Search ............... None
See application file for complete search history.

(56) References Cited

U.S. PATENT DOCUMENTS

| 2005/0181452 A1 | 8/2005 | Westwick et al. |
| 2006/0026702 A1 | 2/2006 | Rockman et al. |
| 2006/0029983 A1 | 2/2006 | Oakley et al. |
| 2006/0188944 A1 | 8/2006 | Barak et al. |

OTHER PUBLICATIONS

Beaulieu J-M et al. Akt/GSK3 signaling in the action of psychotropic drugs. Annu. Rev. Pharmacol. Toxicol. 2009; 49: 327-347.
Beaulieu JM, Sotnikova TD, Yao WD, Kockeritz L, Woodgett JR, Gainetdinov RR, Caron MG. Lithium antagonized dopamine-dependent behaviors mediated by an AKT/glycogen synthase kinase 3 signaling cascade. Proceedings of the National Academy of Sciences 101(14):5099-5104 (2004).
Beaulieu JM, Sotnikova TD, Marion S, Lefkowitz RJ, Gainetdinov RR, Caron MG. An Akt/β-Arrestin 2/PP2A Signaling Complex Mediates Dopaminergic Neurotransmission and Behavior. Cell 122:261-273 (2005).
Lefkowitz RJ, Shenoy SK. Transduction of Receptor Signals by β-Arrestins. Science 308:512-517 (2005).
Foord SM, Bonner TI, Neubig RR, Rosser EM, Pin JP, Davenport AP, Spedding M, Harmar AJ. International Union of Pharmacology. XLVI. G Protein-Coupled Receptor List. Pharmacological Reviews 57(2):279-288 (2005).
Reiter E, Lefkowitz RJ. GRKs and β-arrestins: roles in receptor silencing, trafficking and signaling. Trends in Endocrinology and Metabolism 17(4):159-165.(2006).

*Primary Examiner*—David S Romeo
(74) *Attorney, Agent, or Firm*—Myers Bigel Sibley & Sajovec, P.A.

(57) ABSTRACT

A method of screening a candidate compound for βArrestin mediated anti-G protein coupled receptor signaling activity is comprises: (a) contacting said candidate compound to a βArrestin signaling complex or a constituent thereof, under conditions in which a signaling complex is formed; and then (b) detecting the presence or absence of disruption of said signaling complex, disruption of said complex indicating said compound has βArrestin mediated anti-G protein coupled receptor signaling activity. Compositions and kits for carrying out the method are also described.

8 Claims, 1 Drawing Sheet

METHODS FOR IDENTIFYING COMPOUNDS THAT REGULATE β-ARRESTIN SIGNALING COMPLEXES

RELATED APPLICATIONS

This application claims the benefit of U.S. Provisional Patent Application Ser. No. 60/699,651, filed Jul. 15, 2005, the disclosure of which is incorporated by reference herein in its entirety.

STATEMENT OF GOVERNMENT SUPPORT

This invention was made with Government support under grant numbers DA-13511, NS-19576, and MH-40159 from the National Institutes of Health. The US Government has certain rights to this invention.

FIELD OF THE INVENTION

The present invention concerns methods of screening for compounds having anti-βArrestin mediated signaling activity.

BACKGROUND OF THE INVENTION

There are presently no pharmacological methods to regulate the formation of βArrestin based signaling complexes without affecting G-protein mediated signaling. Current drugs acting on GPCRs are either receptor agonists (bromocriptine, apomorphine) receptor antagonists (haloperidol, beta-adrenergic blocking agents) or indirect agonists (amphetamines, selective serotonin reuptake inhibitor, methylphenidate), that exert their effects on all components of GPCR signaling. As a result of this lack of signaling-mechanism specificity, current compounds can alleviate symptoms resulting from aberrant βArrestin-based signaling while leading to the development of side effects through concomitant deregulation of G-protein mediated signaling. Conversely, the therapeutic action of these drugs can also come from their action on G-protein mediated signaling while side effects would arise from noxious effects of βArrestin-based signaling complexes. Thus, alone or in combinations, drugs acting on the formation of βArrestin-based signaling complexes provide more specific ways to regulate GPCR signaling then currently available compounds. A variation of this theme would be compounds that would bind to GPCRs specifically but would act differentially as agonists or antagonists for one response (i.e. G protein-dependent signaling) and not the other (βArrestin-dependent signaling) and vice versa. No such compounds are known yet for receptors like those for dopamine, serotonin, adrenergic alpha, beta, but could be identified by the methods outlined herein.

SUMMARY OF THE INVENTION

A first aspect of the present invention is a method of screening a candidate compound for anti-βArrestin mediated G protein coupled receptor (GPCR) signaling activity, comprising: (a) contacting said candidate compound to a βArrestin signaling complex or a constituent thereof, said signaling complex comprising, as constituents, βArrestin and from one to three signaling proteins, (in one example, by contacting said compound to at least one of Akt, βArr-2, PP2A, or a signaling complex thereof); and then (b) detecting the presence or absence of disruption of the signaling complex, disruption of said complex indicating said compound has anti-βArrestin mediated G protein coupled receptor signaling activity.

A second aspect of the present invention is a composition (e.g., an aqueous composition) comprising, consisting of, or consisting essentially of βArrestin and from one to three signaling proteins (e.g., a composition comprising, consisting of or consisting essentially of at least one, two, or all three of Akt, βArr-2, PP2A), or a signaling complex thereof, which composition is useful for carrying out the methods described herein in vitro.

A further aspect of the invention is a kit comprising a composition as described herein in aqueous or lyophilized form, optionally but preferably including instructions for carrying out a method as described herein.

The foregoing and other objects and aspects of the present invention are explained in greater detail in the drawings herein and the specification set forth below.

DETAILED DESCRIPTION OF THE PREFERRED EMBODIMENTS

Figure 1:
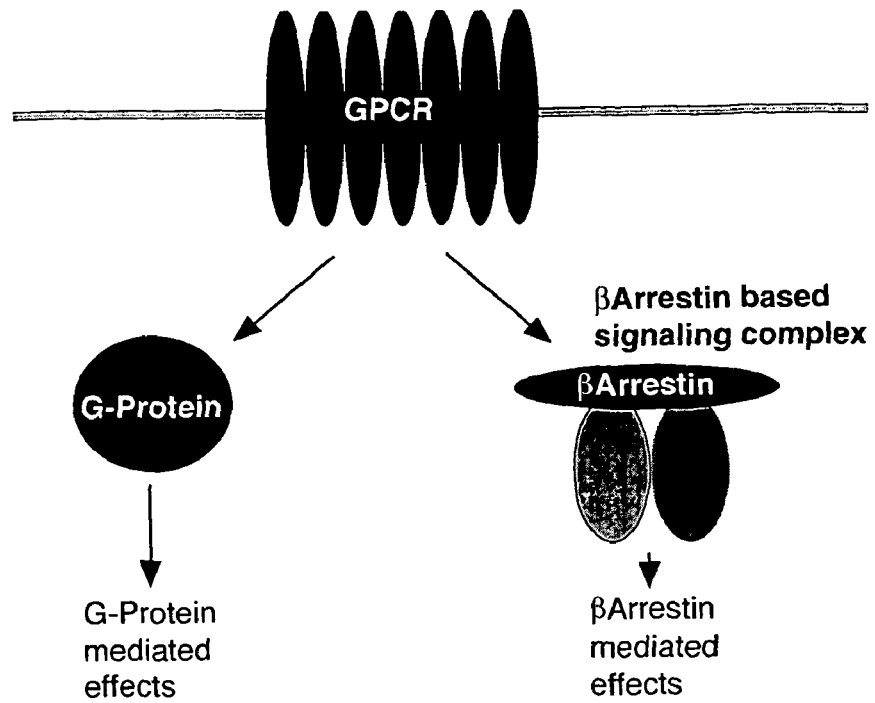
FIG. 1. Dual mechanisms of GPCR signaling. Following activation, GPCR can signal through parallel pathways. The canonical pathway of GPCR signaling involves G-proteins and leads to one set of physiological response. The alternative pathway involves the formation of β-based signaling complexes and leads to a separate set of physiological responses.

Cells that may be used to carry out the present invention include but are not limited to central nerve cells, peripheral nerve cells, skin cells, gastrointestinal cells, muscle cells, vascular cells, lymphocytes, neutrophils, macrophages, fibroblasts, tumor cells, osteoblasts and osteocytes whether cells are in culture or in a whole animal.

Anti-G protein coupled receptor signaling activity that may be detected or determined by the methods of the invention involves any of the more than 800 GPCR (Int Union Pharmacol) and include but are not limited to anticancer, antidopaminergic, antiserotoninergic, antimuscarinic, antiadrenergic, anti-peptide hormone signaling (for example, angiotensin, vasopressin) and antiopiate activity.

"Mammalian" as used herein with respect to proteins or peptides may be that of any mammalian species, including but not limited to cat, dog, rabbit, primate (human, monkey, etc.), and rodent (mouse, rat, etc.).

βArrestin, Beta-arrestin, and like descriptions thereof are known and as used herein include β-Arrestin 1 and β-Arrestin 2. βArrestins as used herein may be from any suitable species, preferably mammalian. For example, Beta-arrestin-2 as used herein may be from any suitable species, and is preferably mammalian. Mammalian beta-arrestin-2 is known, including that from mouse (see, e.g., REFSEQ: accession NM_145429.1 and Ferrari, S. L., et al., Endocrinology 146 (4), 1854-1862 (2005); swissprot: locus ARRB2_MOUSE, accession Q91Y14 and Strausberg, R. L. et al., Proc. Natl. Acad. Sci. U.S.A. 99 (26), 16899-16903 (2002)) and that from human (see, e.g., REFSEQ: accession NM_199004.1 and Feng, Y. H. et al., Am. J. Physiol., Cell Physiol. 288 (6), C1342-C1356 (2005)).

βArrestin signaling complexes (sometimes also referred to as cytoplasmic signaling complexes) are known. Examples include but are not limited to those described in R. Lefkowitz and S. Shenoy, Transduction of Receptor Signals by β-Arrestins, *Science* 308, 512-517 (22 Apr. 2005) and in E. Reiter and R. Lefkowitz, GRKs and β-arrestins: roles in receptor silencing, trafficking and signaling, *TRENDS in Endocrinology and Metabolism* 17, 159-165 (2006). Still other examples are given herein. Particular examples include but are not limited to complexes comprising, consisting of or consisting essentially of βArrestin in combination with one, two or three signaling molecules such as Akt, PP2A, GSK3, Cdk5, Erk1, Erk2, MEK, Src, IkappaB, NF Kappa B, Raf, Rho, JNK, CREB, Yes, HCK etc.

AKT as used herein may be from any suitable species, and is preferably mammalian. Mammalian AKT (AKT1, AKT2 and AKT3) is known, including that from mouse (see, e.g., swissprot: locus AKT1_MOUSE, accession P31750 and Bellacosa, A., et al., Oncogene 8 (3), 745-754 (1993); swissprot: locus AKT2_MOUSE, accession Q60823; class: standard and Altomare, D. A. et al., Oncogene 11 (6) 1055-1060 (1995); swissprot: locus AKT3_MOUSE, accession Q9WUA6; class: standard and Brodbeck, D. et al., J. Biol. Chem. 274 (14) 9133-9136 (1999)) and that from human (see, e.g., swissprot: locus AKT1_HUMAN, accession P31749; class: standard and Jones, P. F. et al., Proc. Natl. Acad. Sci. U.S.A. 88 (10), 4171-4175 (1991); swissprot: locus AKT2_HUMAN, accession P31751; class: standard and Jones, P. F. et al., Cell Regul. 2 (12), 1001-1009 (1991); swissprot: locus AKT3_HUMAN, accession CAB53537 and Masure, S. et al. Eur. J. Biochem. 265(1), 353-360 (1999); swissprot: locus AKT3_HUMAN, accession AAH20479 and Strausberg, R. L. et al. Proc. Natl. Acad. Sci. U.S.A. 99(26), 16899-16903 (2002)).

PP2A as used herein may be from any suitable species, and is preferably mammalian. Mammalian PP2A is known, including that from mouse (see, e.g., swissprot: locus 2A5R_MOUSE, accession Q9Z176; and Voorhoeve, P. M., et al., Oncogene 18 (2), 515-524 (1999); swissprot: locus P2AA_MOUSE, accession P63330; class: standard and Hsu, W. et al. J. Biol. Chem. 274 (6), 3439-3445 (1999); REFSEQ: accession NM_017374.2 and Gotz, J. et al. Mech. Dev. 93 (1-2), 83-93 (2000)) and that from human (see, e.g., swissprot: locus 2ACC_HUMAN, accession Q9Y5P8; class: standard and Yan, Z. et al., Mol. Cell. Biol. 20 (3), 1021-1029 (2000); swissprot: locus 2A5D_HUMAN, accession Q14738; class: standard and McCright, B. et al., J. Biol. Chem. 271 (36), 22081-22089 (1996); swissprot: locus 2ACA_HUMAN, accession Q06190; class: standard and Hendrix, P. et al., J. Biol. Chem. 268 (20), 15267-15276 (1993); swissprot: locus P2AA_HUMAN, accession P67775; class: standard and Virshup, D. M. et al. EMBO J. 8 (12), 3891-3898 (1989); swissprot: locus P2AB_HUMAN, accession P62714; class: standard and Ogris, E. et al. J. Biol. Chem. 274 (20), 14382-14391 (1999)).

Heterologous cellular system as used herein designate cellular cultures made on cell lines originating from different tissues and species including but not restricted to mammalian, insect, fish etc such as HEK293, NIH3T3, U2OS, PC12, Neuro2A, WEHI3B, SW13, etc or new cells cultures derived from animal tissues.

Methods to Detect βArrestin 2/Akt/PP2A Complexes.

The presence or absence of complexes as described herein can be carried out in vitro or in vivo by any suitable method, numerous variations of which will be apparent to those skilled in the art.

A first method can be the ability of any agents to interfere with the presence of the complex in the brain of an animal such as a mouse, in particular in the striatum.

A second method can be the ability of any agents to interfere or enhance the interaction of βarrestin2/Akt/PP2A in an heterologous cellular system such as HEK 293 or U2OS cells in which a tagged βarrestin 2 construct has been transfected and the ability of βarrestin 2 to interact with Akt or PP2A is assessed using an antibody to the tag using any appropriate detection method.

A third method encompasses a procedure in which the interaction of βarrestin 2 and Akt or PP2A can be assessed in a cellular system as above and measure by direct readout of the interaction such that the energy of a tagged βarrestin 2 (i.e. CFP, Renilla luciferase etc) donor is transmitted to an acceptor such as an Akt or PP2A molecule tagged with YFP upon interaction of βarrestin2 and Akt or PP2A. Such method is referred as fluorescence energy transfer (FRET) or bioluminescence energy transfer (BRET) in the case that the donor is Renilla luciferase.

In all cases the complex can be modulated by activation or inhibition of receptors such as D2 dopamine receptors, which are members of the large family of G protein coupled receptors. Thus, any compound including but not limited to agonists or antagonists can be tested for their ability to interfere or stimulate the interaction of βarrestin2/Akt/PP2A granted that such a receptor has been expressed in the same cell as these reporter molecules.

Utility

The present invention provides a means to screen for compounds that have anti-βArrestin mediated G protein coupled receptor signaling activity, which are in turn useful as drug candidates and new methods of treating disorders associated with G protein coupled receptors (as demonstrated by the identification of a known drug, lithium, in a screen of the present invention).

Regulation of βArrestin-based signaling complexes offers a new modality to regulate GPCR signaling and can be of used in the treatment of human or animal disorders associated with aberrant GPCR functions. Moreover, the present invention provides a method to develop or screen for more specific drugs that allow managing symptoms associated with βArrestin-based signaling while avoiding the development of side effects arising from concomitant deregulation of G protein-mediated signaling.

Conversely, co-administration of a drug disrupting βArrestin-based signaling along with agonist/antagonist of GPCR provides a method to avoid the development of βArrestin-based signaling mediated side effects resulting from the treatment of patients with GPCR agonists or antagonists. The present invention provides a means to screen for such compounds.

The present invention is explained in greater detail in the following non-limiting Examples.

Experimental

Here we describe methods for identifying pharmacological compounds to regulate the formation of β-arrestin mediated signaling complexes in vivo. G protein-coupled receptors (GPCR) such as dopamine receptors mediate a myriad of physiological functions through canonical G protein-dependent signaling pathways and serve as targets for many therapeutics agents. Recent evidence from cell culture systems have shown that apart from their action on G-proteins, GPCR also mediate part of their signaling functions by acting through the formation of signaling complexes that utilizes β-arrestin1 or β-arrestin2 as scaffolding intermediates. We recently provided in vivo validation of this new paradigm of GPCR signaling by uncovering a novel pathway for dopamine receptor signaling that involves β-arrestin2 in the brain of living animals (see J.-M. Beaulieu, T, Sotnikova, S. Marion, R. Lefkowitz, R. Gainetdinov, and M. Caron, An Akt/β-Arrestin 2/PP2A Signaling Complex Mediates Dopaminergic Neurotransmission and Behavior, *Cell* 122, 1-13 (Jul. 29, 2005), the disclosure of which is incorporated by reference herein). In this new pathway, β-arrestin 2 acts as a signaling intermediate that scaffolds a complex containing PP2A to inactivate Akt and promote locomotor hyperactivity in mice. The existence of β-arrestin-based signaling in vivo, indicate that GPCR exert their function by acting on two distinct types of signaling mechanisms involving either G-protein or β-arrestins (FIG. 1).

Figure 2:
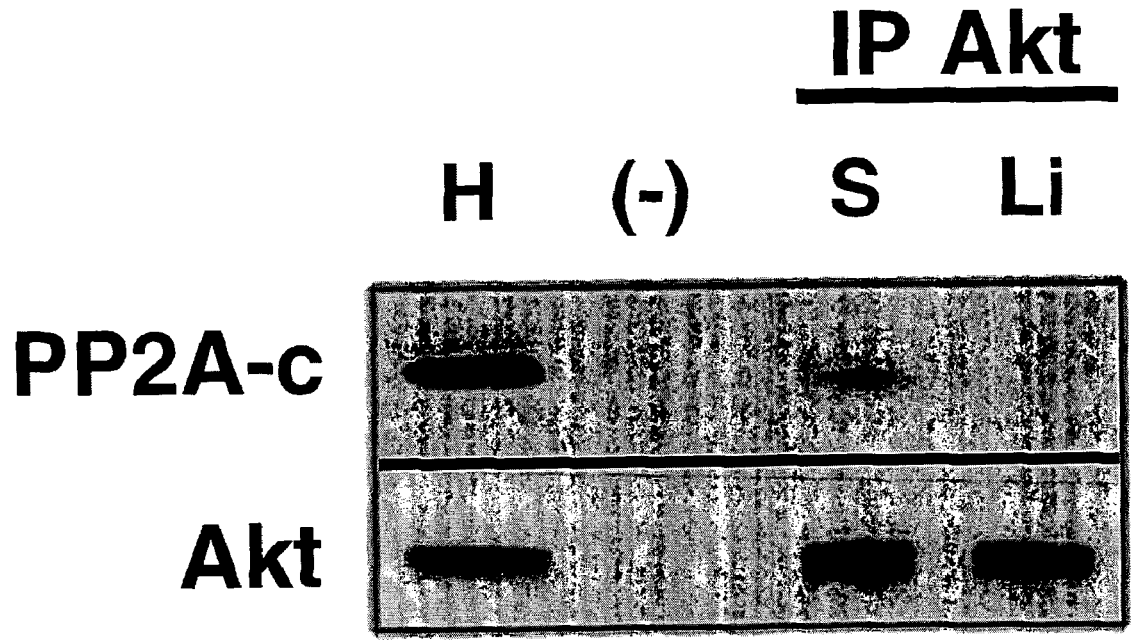
FIG. 2. Disruption of the Akt/βArr-2/PP2A signaling complex by lithium in the mouse striatum. Mice (WT C57 B16) were treated either with saline (S) or lithium chloride, 200 mg/kg i.p. (Li). Striata were dissected out 30 min post-injection and Akt was immunoprecipitated. Lithium treatment fully abolished the βArr-2 mediated interaction of Akt and PP2A.

We used the Akt/βArr-2/PP2A signaling complex (see, e.g., J.-M. Beaulieu et al., supra), to screen for compounds that can modulate the formation of βArrestin-based signaling complexes without affecting G-protein mediated signaling. We have previously shown that lithium chloride antagonizes the behavioral actions dopamine in mice without affecting dopamine receptor G-protein mediated signaling functions (Beaulieu et al., Proc Natl Acad Sci USA. 101(14): 5099-5104 (2004)). To evaluate the action of lithium on the formation of the Akt/βArr-2/PP2A signaling complex, we administered either saline or LiCl (200 mg/kg, i.p.) to normal mice and used anti-Akt antibodies to immunoprecipitate the Akt/βArr-2/PP2A signaling complex from the striatum of these animals. As shown in FIG. 2, treatment of the animals with LiCl totally prevented the co-immunoprecipitation of PP2A with Akt thus indicating that lithium disrupts the formation of the Akt/βArr-2/PP2A signaling complex in vivo.

In the specific example given here, disruption of the Akt/βArr-2/PP2A signaling complex regulated by D2-class dopamine receptors can be used for the treatment of psychiatric and neurological conditions including but not limited to: schizophrenia, attention deficit hyperactivity disorder (ADHD), bipolar disorder, depression, anxiety, tourette syndrome, epilepsy, addiction, mood disorders, obsessive compulsive disorder, Parkinson disease, Huntington diseases and side effects related with the management of these disorders (eg: diskinesia and tardive dyskinesia). Moreover, due to the broad range of physiological functions mediated by GPCRs, the present invention can also have applications in the management of non-psychiatric disorders such as cancer, diabetes, cardiovascular disease and immune system dysfunctions.

The foregoing is illustrative of the present invention, and is not to be taken as limiting thereof. The invention is defined by the following claims, with equivalents of the claims to be included therein.

That which is claimed is:

1. A method of screening a candidate compound for anti-βArrestin-2 mediated G protein coupled receptor signaling activity, comprising:
   (a) contacting said candidate compound to a βArrestin-2 signaling complex or a constituent thereof, said signaling complex comprising as constituents βArrestin 2, Akt and PP2A, under conditions in which a signaling complex of said constituents is formed in the absence of said candidate compound; and then
   (b) detecting the presence or absence of disruption of a said signaling complex, disruption of said complex indicating said compound has anti-βArrestin-2 mediated G protein coupled receptor signaling activity.

2. The method of claim 1, wherein said contacting step is carried out in vitro.

3. The method of claim 1, wherein said contacting step is carried out in a heterologous cell system.

4. The method of claim 1, wherein said contacting step is carried out in vivo in mammalian cells, and wherein said cells are grown in culture or a host animal.

5. The method of claim 4, wherein said cells are central nerve cells, peripheral nerve cells, skin cells, gastrointestinal cells, muscle cells, vascular cells, lymphocytes, neutrophils, macrophages, fibroblasts, tumor cells, osteoblasts and osteocytes.

6. The method of claim 1, wherein said detecting step is carried out in vitro or in vivo.

7. The method of claim 1, wherein said anti-G protein coupled receptor signaling activity is selected from the group consisting of anticancer, antidopaminergic, antiserotoninergic, antimuscarinic, antiadrenergic, anti-peptide hormone signaling and antiopiate activity.

8. The method of claim 1, wherein said anti-G protein coupled receptor signaling activity is anti-peptide hormone signaling activity selected from the group consisting of angiotensin and vasopressin signaling activity.

* * * * *